United States Patent [19]

Tenmyo et al.

[11] Patent Number: 4,803,224

[45] Date of Patent: Feb. 7, 1989

[54] ANTIVIRAL ANTIBIOTIC COMPLEX

[75] Inventors: Osamu Tenmyo, Yokohama; Hiroaki Ohkuma, Tokyo; Masataka Konishi, Kawasaki, all of Japan

[73] Assignee: Bristol-Myers Company, New York, N.Y.

[21] Appl. No.: 857,878

[22] Filed: May 1, 1986

[51] Int. Cl.$^4$ .................. C07C 103/50; A61K 31/195
[52] U.S. Cl. ..................................... 514/563; 435/129; 562/561
[58] Field of Search ........................ 562/561; 514/563

[56] References Cited

PUBLICATIONS

Shima, Agric. Biol. Chem., 45, pp. 2503–2508 (1981).

Primary Examiner—Michael L. Shippen
Attorney, Agent, or Firm—David M. Morse

[57] ABSTRACT

There is disclosed an antibiotic complex designated as BU-2231 V which is produced by fermentation of a BU-2231-producing strain of *Streptoalloteichus hindustanus*, ATCC 31158. Complex BU-2231 V is recovered and purified from the fermentation broth by use of ion exchange chromatography techniques. Structural analysis shows that the complex is a mixture of components which are $\gamma$-homopolymers of D-$\alpha,\gamma$-diaminobutyric acid having an average molecular weight of from about 5,100 to about 5,200. BU-2231 V has been found to be effective to inhibit growth of various Gram-positive and Gram-negative bacteria and of the herpes simplex virus.

2 Claims, 2 Drawing Sheets

HPLC OF BU-2231V

Toyo Soda TSK Gel 3000 SW (7.5 × 600 mm)
M/15 phosphate buffer, pH 7.0
0.7 ml/minute, UV at 210 nm

ANTIVIRAL ANTIBIOTIC COMPLEX

BACKGROUND OF THE INVENTION

1. Field of the Invention

This invention relates to a new antiviral antibiotic complex, to its production and recovery, and to its use to inhibit the growth of various Gram-positive and Gram-negative bacteria and of viruses, representative of which is the herpes simplex virus.

2. Description of the Prior Art

H. Kawaguchi et al., U.S. Pat. No. 4,051,237, disclose the production and recovery of the BU-2231 antibiotic complex and separation of two glycopeptide antibiotics, BU-2231 A and BU-2231 B, from the complex, by fermentation of a BU-2231-producing strain of *Streptoalloteichus hindustanus* (ATCC 31158) followed by treatment using ion exchange chromatographic techniques to separate the co-produced aminoglycoside complex from the desired BU-2231 complex.

SUMMARY OF THE INVENTION

This invention is a new water-soluble antiviral antibiotic complex designated BU-2231 V which is produced by fermenting a BU-2231-producing strain of *Streptoalloteichus hindustanus*, most preferably the strain *Streptoalloteichus hindustanus* ATCC 31158 or a mutant thereof, in an aqueous fermentation culture nutrient medium containing assimilable sources of nitrogen and carbon under submerged aerobic conditions until a substantial amount of the glycopeptide antibiotic complex of BU-2231 containing components designated BU-2231 A and BU-2231 B is produced by the organism in the fermentation culture nutrient medium. The antibiotic components produced by the fermentation of the above organism are recovered by separating the water-insoluble material from the fermentation broth to obtain a fermentation supernatant liquid containing the water-soluble antibiotic components and the resulting supernatant liquid is applied to a cationic exchange resin to adsorb the antibiotic components. The new antiviral antibiotic complex, BU-2231 V, is isolated by subjecting the resin having adsorbed thereon the antibiotic components to selective gradient elution.

DETAILED DESCRIPTION OF THE INVENTION

Figure 1:
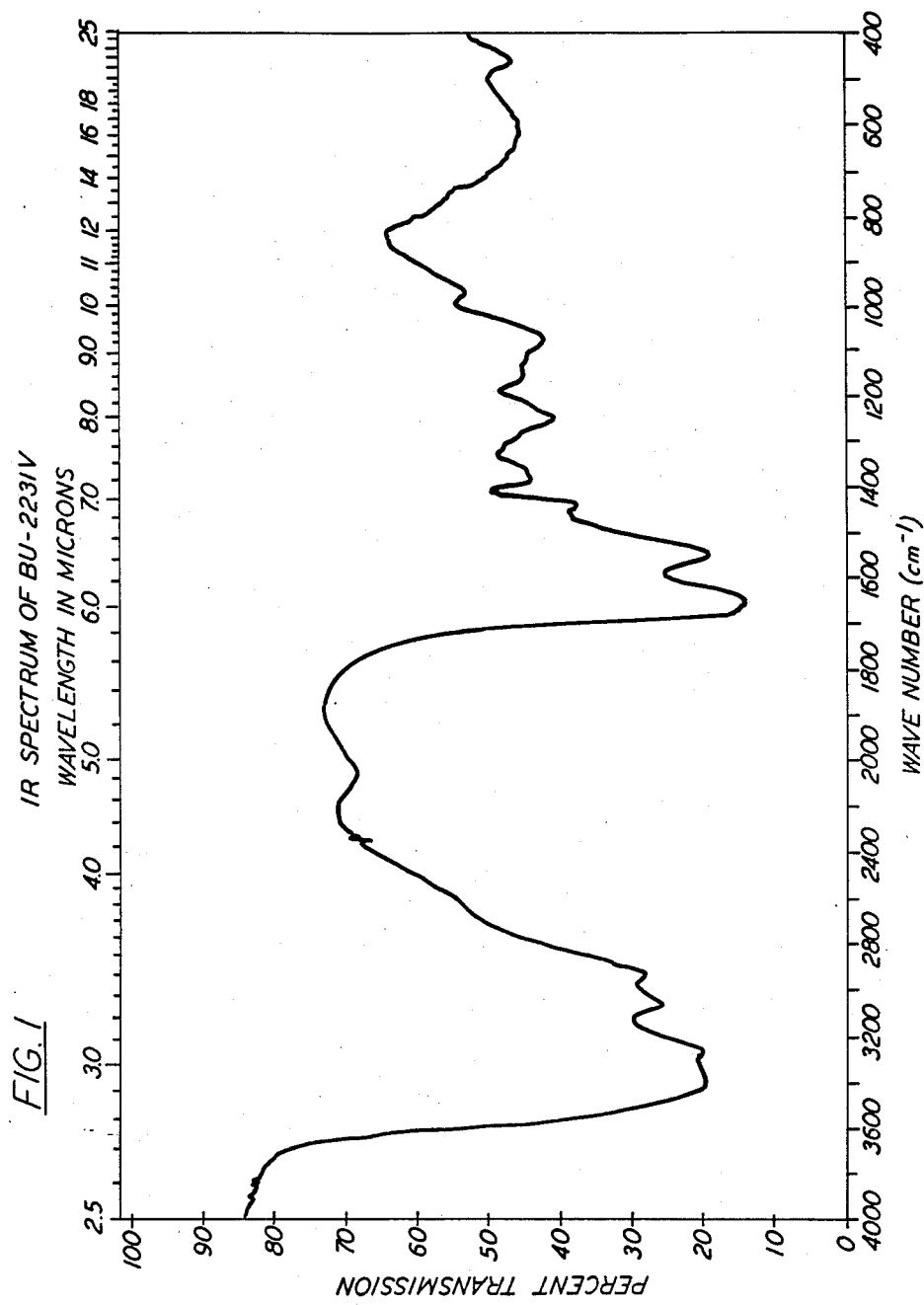
FIG. 1 shows the infrared (IR) absorption spectrograph of BU-2231 V which pelleted in potassium bromide. This IR spectrum indicates amino (3400 cm$^{-1}$) and amide (1640 and 1540 cm$^{-1}$) functional groups.

In one aspect, the present invention is a new antiviral antibiotic complex, designated BU-2231 V, which is produced by fermenting a BU-2231-producing strain of *Streptoalloteichus hindustanus*, most preferably the strain *Streptoalloteichus hindustanus* ATCC 31158.

In another aspect, this invention is a pharmaceutical composition of BU-2231 V.

In still another aspect, this invention is a process for producing the novel antiviral antibiotic complex, BU-2231 V.

In yet another aspect, this invention is a process for inhibiting the growth of at least one of Gram-positive bacteria, Gram-negative bacteria, and viruses comprising contacting such bacteria and viruses with a growth-inhibitory effective amount of the novel antibiotic complex, BU-2231 V.

I. The Microorganism

The morphological, cultural, and physiological characteristics of the most preferred strain *Streptoalloteichus hindustanus* ATCC 31158 used to produce the novel antiviral antibiotic according to the present invention is described in U.S. Pat. No. 4,051,237 issued Sept. 27, 1977.

II. Preparation, Isolation, and Purification of the Antibiotic

The process for producing the antiviral antibiotic complex BU-2231 V according to the present invention comprises the steps of:

(a) cultivating *Streptoalloteichus hindustanus* ATCC 31158 in an aqueous fermentation culture nutrient medium containing assimilable sources of nitrogen and carbon under submerged aerobic conditions until a substantial amount of (i) the glycopeptide antibiotic complex of BU-2231 containing components designated BU-2231 A and BU-2231 B is produced and (ii) the aminoglycoside antibiotic complex designated as nebramycin factors is co-produced by the organism in the fermentation culture medium;

(b) separating the mycelium and other undissolved residues from the fermentation culture medium to obtain a supernatant liquid which contains antibiotic activity;

(c) adsorbing the antibiotic activity components contained in the supernatant liquid from step (b) on a first cationic exchange resin;

(d) separating the more strongly bound and more weakly bound antibiotic activity components adsorbed to the first cationic resin from step (c) by selective gradient elution techniques which will displace those antibiotic activity components which are more weakly bound from the first cationic exchange resin into a first eluate while leaving bound to the first resin those BU-2231 complex antibiotic activity components which are more strongly bound;

(e) adsorbing the antibiotic activity components contained in the first eluate from step (d) on a second cationic exchange resin;

(f) separating the antibiotic activity components adsorbed to the second cationic resin in step (e) by selective gradient elution techniques employing a second eluant having sufficient base strength to displace the aminoglycoside antibiotic complex from the second resin followed by employing a third eluant having sufficient base strength to displace the antibiotic activity components retained adsorbed to the second resin after elution with the second eluant; and (g) recovering from the third eluate from step (f) the antiviral antibiotic complex, BU-2231 V, by at least one of conventional adsorption techniques and crystallization techniques.

The assimilable carbon source for use in the aqueous fermentation culture medium may be a carbohydrate such as, for example, glucose, ribose, galactose, fructose, mannose, sucrose, lactose, soluble starch and glycerol to name a few.

The assimilable nitrogen source for use in the aqueous fermentation culture medium may be any one of such conventionally known sources including fish meal, soybean meal, corn steep liquor, peptones, meat extract, peanut flour, yeast extract, and ammonium salts to name but a few.

Inorganic salts such as sodium chloride, potassium chloride, magnesium sulfate, calcium carbonate, phosphates, and the like may be added if desired. In addition, trace elements such as copper, manganese, iron, zinc and the like may be added if desired or they may be supplied as minor or trace impurities of other constituents in the fermentation media.

The incubation temperature may be any temperature at which a BU-2231-producing strain is able to grow. Preferably the incubation temperature is about 20-54 deg. C., more preferably about 25-35 deg. C., most preferably about 27-32 deg. C.

A neutral or nearly-neutral initial pH, e.g. pH about 6-7, is preferably employed in the fermentation media, and production of the antibiotic by fermentation is generally carried out for a period of about 2-7 days. Ordinarily, optimum production is achieved in about 3-5 days. For preparation of relatively small amounts of antiviral antibiotic complex, shake flasks and surface culture can be employed whereas for relatively large amounts, submerged aerobic culture in sterile fermentation tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermentation medium. Further agitation of the medium may be provided by a mechanical impeller and an anti-foaming agent such as is conventional in the art, e.g. lard oil, may be added as needed.

The production of BU-2231 in the fermentation medium may be followed readily during the course of fermentation by the paper disc-agar diffusion method using *Bacillus subtilis* PCI-219 and *Mycobacterium smegmatis* strain M6-3 as test organisms. The BU-2231 A and BU-2231 B components of BU-2231 antibiotic complex as well as the co-produced aminoglycoside complex (also referred to as the "nebramycin factors" or "nebramycin components") are believed to be active against *B. subtilis* but only the BU-2231 A and B comppnents show activity against *Mycobacterium smegmatis* strain M6-3.

After optimum fermentation broth potency has been obtained (as determined by the above-described assay method), the mycelium and undissolved residues are separated from the fermentation broth by conventional means such as filtration and centrifugation to obtain a supernatant liquid (or filtrate) which contains antibiotic activity. The components having antibiotic activity can be recovered from the supernatant liquid by employing conventional adsorption techniques. The adsorbents which can be employed most advantageously are the weakly acidic cationic exchange resins including, for example, those resins such as the Amberlite ® IRC-50 and Amberlite ® CG-50 resins (Amberlite is a trademark owned by the Rohm and Haas Company, Philadelphia, Pa.) commercially available from the Rohm and Haas Company and nonionic macroreticular polymer resins including, for example, Diaion ™ HP-20 resin (Diaion is a trademark owned by Mitsubishi Chemical Industries, Ltd., Tokyo, Japan) commercially available from Nippon Rensui Co., Japan. In one, preferred embodiment, the supernatant liquid, neutralized if necessary to pH 7, is passed through a column packed with a cationic exchange resin such as Amberlite IRC-50 in the ammonium form to adsorb from the supernatant liquid the components having antibiotic activity. These components having antibiotic activity include those antibiotic substances BU-2231 complex and the aminoglycoside complex ("nebramycin factors") described in the above-mentioned U.S. Pat. No. 4,051,237 as well as the antiviral antibiotic complex, BU-2231 V, according to the present invention. After washing this resin having antibiotic activity components adsorbed thereon with water, this resin is subjected to selective gradient elution techniques, wherein there is employed 0.01N and 0.25N aqueous ammonium hydroxide successively, which will displace those antibiotic activity components that are weakly bound to the resin while the more strongly bound components are retained bound to the resin. Such weakly bound antibiotic activity components include the nebramycin factors and the BU-2231 V complex according to the present invention whereas the more strongly bound antibiotic activity components include the BU-2231 complex and the BU-2231 A and B components thereof. Of course, the BU-2231 complex can be purified as described in U.S. Pat. No. 4,051,237.

It has been discovered that the first eluate from the above-described selective gradient elution of the resin having antibiotic activity components adsorbed thereon can be passed through another column packed with a second cationic exchange resin such as Amberlite CG-50 in the ammonium form to adsorb from the eluate the components therein having antibiotic activity. The components having antibiotic activity in the above-described first eluate include the aminoglycoside complex ("nebramycin factors") as well as the antiviral antibiotic complex, BU-2231 V, according to the present invention. After washing this second resin having antibiotic activity components adsorbed thereon with water, this second resin is subjected to a second selective gradient elution with, as a second eluant, an aqueous solution of ammonium hydroxide having sufficient base strength to displace the aminoglycoside antibiotic complex that is co-produced in the fermentation step.

The resulting second eluate has been found to contain substantially all of the aminoglycoside antibiotic complex components. Then, the second resin is further eluted with, as a third eluant, an aqueous ammonium hydroxide solution having sufficient base strength to displace the antibiotic activity components which are retained adsorbed to the second resin following the displacement of substantially all of the aminoglycoside antibiotic complex components. A 0.4N aqueous ammonium hydroxide solution has been found to be especially advantageous to displace such retained antibiotic activity components. The resulting third eluate, free from BU-2231 antibiotic complex and aminoglycoside antibiotic complex components, is concentrated to provide a brownish solid of crude new antibiotic activity component. The new crude antibiotic activity component is further purified by one of conventional adsorption, gel filtration, and crystallization techniques or a combination of such techniques. For example, further purification may be performed especially advantageously by dissolving the crude solid in water, filtering the resulting solution, adjusting the pH of the filtrate to about 9, and passing the filtrate having pH 9 through a column packed with a nonionic resin such as, for example, Diaion TM HP-20 resin to adsorb the antibiotic activity component(s) from the filtrate. The resin having antibiotic activity component-containing filtrate loaded thereon is washed with water and then eluted with an aqueous solution containing 60% (volume %) of methanol. The resulting antibiotic activity-containing eluate is concentrated in vacuo to provide a semi-pure solid. This semi-pure solid is then applied to a column packed with silica gel Wako TM C-200 brand silica gel commercially available from Wako Pure Chemical Industries Ltd., Japan) and the silica gel column is first eluted with chloroform-methanol-28% aqueous ammonium hydroxide solution-water (1:4:2:1) and then with the upper layer of chloroform-methanol-28% aqueous ammonium hydroxide solution (1:1:1). The eluate fractions having antibiotic activity are combined and concentrated in vacuo. The resulting concentrate is then applied to a column packed with Sephadex TM G-25 resin (Sephadex is a trademark owned by the Pharmacia Fine Chemicals Inc.) and the resin having the antibiotic activity component-containing solid loaded thereon is eluted with water. The eluate therefrom is concentrated in vacuo and lyophilized to obtain pure BU-2231 V complex as a white solid.

Antibiotic complex BU-2231 V produced substantially as described above, specifically as produced according to the actual example which follow, was characterized as described below.

III. Structure Determination

Antibiotic complex BU-2231 V has been found to be a complex of multicomponents with an average molecular weight of 5,700 when determined by gel filtration analysis (Sephadex G-50, reference standards; ovalbumin MW 43,000, chymotrypsinogen 25,000, ribonuclease A 13,700 and tallysomycin A 1,778). A more accurate molecular weight of around 5,100–5,200 was assigned to antibiotic complex BU-2231 V when determined by DNP experiment.

The complex was hydrolyzed with 6N HCl under reflux for 18 hours. The hydrolyzate exhibited the presence of only one ninhydrin positive substance which was identified as $\alpha,\gamma$-diaminobutyric acid (DAB) by TLC (thin layer chromatography) (SiO$_2$, n.BuOH-AcOH-H$_2$O=3:1:1, Rf 0.10 and 10% AcONH$_4$-MeOH-10%NH$_4$OH=9:10:1, Rf 0.30) and amino acid analysis. In order to isolate this amino acid for configurational analysis, the hydrolyzate was chromatographed on Amberlite CG-50 (H$^+$) with elution of 1.0N HCl. The ninhydrin positive fractions were concentrated and the residue was crystallized from aqueous ethanol to afford colorless needles. The optical rotation ($[\alpha]^{26.5}$ : −20 deg., G. A. R. Johnston et al., *Br. J. Pharmac.*, 59, 218-219 (1977) literature value : −19.5 deg.) and the IR (infrared) spectrum of the crystals were identical with those of D-$\alpha,\gamma$-diaminobutyric acid having the structural formula given below.

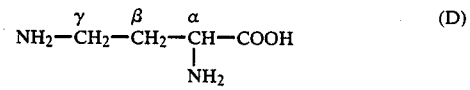

The $^1$H- and $^{13}$C-NMR (nuclear magnetic resonance spectrum) suggested that BU-2231 V is a complex of $\gamma$-homopolymer of D-$\alpha,\gamma$-diaminobutyric acid. The $^1$H-NMR spectrum in D$_2$O indicated the presence of two methylenes ($\delta$: 2.20 ppm, m, $\beta$-CH$_2$ and 3.43 ppm, m, $\gamma$-CH$_2$) and one methine ($\gamma$: 3.60 ppm, t, J : 6.2 Hz, $\alpha$-CH). This methine proton underwent a significant downfield shift (0.48 ppm) upon acidification, indicating that the $\alpha$-amino group is free in the antibiotic molecule. The $^{13}$C-NMR spectrum (D$_2$O) showed four signals at $\delta$: 34.2 (t, $\beta$-CH$_2$), 36.7 (t, $\gamma$-CH$_2$), 53.3 (d, $\alpha$—CH) and 177.1 ppm (CO—). When the spectrum was determined at PD 2.0, the higherfield methylene and the carbonyl carbons demonstrated a clear $\beta$-protonation shift to $\delta$: 31.3 and 170.4 ppm, respectively, supporting the $\alpha$-free amino structure.

Alternatively, the $\gamma$-homopolymer structure was evidenced by dinitrophenylation. Upon treatment with 2,4-dinitrofluorobenzene (DNP) in an aqueous sodium bicarbonate solution, BU-2231 V afforded the DNP-derivative which was hydrolyzed in 0.71N H$_2$SO$_4$. Two DNP-amino acids produced were separated and purified by preparative TLC. The major one (m.p. 204–205 deg. C.) was identified as $\alpha$-DNP-$\alpha,\gamma$-diaminobutyric acid ($\alpha$-DNP-DAB) (see S. Wilkinson et al., *J. Chem. Soc.*, 4107 (1964)) and the minor one (m.p. 123–124 deg. C.) as $\alpha,\gamma$-di-DNP-$\alpha,\gamma$-diaminobutyric acid ($\alpha,\gamma$-DNP-DAB) (see S. Wilkinson *ibid*, and K. R. Rao et al., *J. Amer. Chem. Soc.*, 76, 1328 (1954)) in comparison with authentic samples.

The $\alpha,\gamma$-DNP-DAB should be derived from the N-terminal moiety and $\alpha$-DNP-DAB from the remaining parts of BU-2231 V molecule. Since no trace of $\gamma$-DNP-DAB and free $\alpha,\gamma$-diaminobutyric acid was found in the hydrolyzate, the result of the DNP experiment indicated a linear, $\gamma$-homopolymeric structure of D-$\alpha,\gamma$-diaminobutyric acid for BU-2231 V.

It has been reported that 2,4-dinitrophenyl derivatives of L-lysine partly decomposed during acid hydrolysis (see S. Shima and H. Sakai, *Agr. Biol. Chem.*, 45, 2503 (1981). Under the hydrolytic condition used for DNP-2231 V (0.71N, H$_2$SO$_4$, reflux for 10 hours), 26.9% of authentic $\alpha,\gamma$-DNP-DAB and 47.0% of authentic $\alpha$-DNP-DAB were decomposed. Taking into consideration these decomposition rates, the ratio of $\alpha,\gamma$-DNP-DAB and $\alpha$-DNP-DAB produced by acid hydrolysis of DNP-BU-2231 V was calculated as 1:50.3, indicating an average molecular weight of 5,130 (5,100–5,200) for the antibiotic.

Thus, antiviral antibiotic complex BU-2231 V has been characterized as described above and shown to be a $\gamma$-homopolymer of D-$\alpha$, $\gamma$-diaminobutyric acid having the structure represented by the following formula:

BU-2231 V

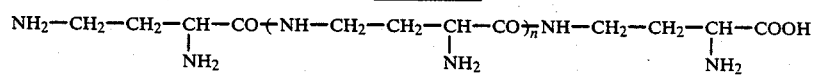

n = 49–50 (average)

Figure 2:
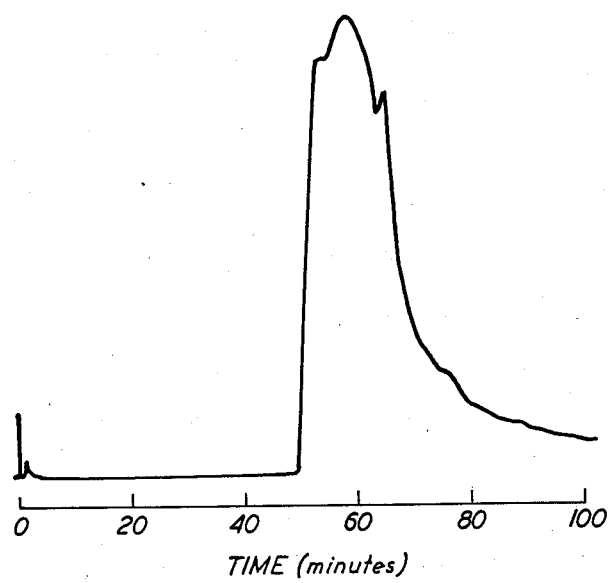
FIG. 2 shows the high pressure liquid chromatography scan of BU-2231 V which depicts the several components in the BU-2231 V complex.

Physico-chemical data of BU-2231 V were determined and the results are summarized in Table 1. BU-2231 V is readily soluble in water and dimethyl sulfoxide, slightly soluble in methanol and ethanol but practically insoluble in other organic solvents. It gives positive response to ninhydrin, Dragendorff, Rydon-Smith reagents and negative response to ferric chloride and anthrone reagents. BU-2231 V shows no specific absorption in the UV and visible region. The IR spectrum of BU-2231 V (FIG. 1) indicated amino (3400 cm$^{-1}$) and amide (1640 and 1540 cm$^{-1}$) functionalities. BU-2231 V consists of several components as depicted in the HPLC (FIG. 2).

TABLE 1

| Physico-chemical properties of BU-2231V | |
|---|---|
| Nature | White amorphous solid |
| M.p. | 165–167° C. |
| $[\alpha]_D^{25}$ | −19° (c 1.0, H$_2$O) |
| Microanalysis | Calcd         Found |
| | $C_4H_8N_2O.\tfrac{1}{3}H_2CO_3$ |
| | C 43.08       C 43.80 |
| | H 7.23        H 7.84 |
| | N 23.18       N 23.00 |
| Molecular weight | 5,700 (Sephadex G-50 gel filtration chromatography) |
| | 5,100–5,200 (DNP method) |
| TLC, SiO$_2$ | Rf 0.02 CHCl$_3$—MeOH-28% NH$_4$OH—H$_2$O (1:4:2:1) |
| | 0.72 CHCl$_3$—MeOH-28% NH$_4$OH (1:1:1, upper layer) |

IV. Biological Activity (1) Antiviral Activity

Antiviral activity of BU-2231 V was assessed using the herpes simplex virus type I (HSV-1)-Vero cell system by the plaque reduction assay and the dye-uptake assay (C. McLaren et al., *Antiviral Research*, 3, 223 (1983)). ε-poly-L-lysine (S. Shima and H. Sakai, *Agr. Biol. Chem.*, 41, 1807 (1977)), a structurally related compound produced by *Streptomyces* No. 346 (kindly provided by Prof. H. Sakai of University of Osaka Prefecture) and two types of α-poly-L-lysine (MW 3,500 and 25,000) were comparatively tested as the reference compound. The results are shown in Table 2 together with their cytotoxicity against the host cells. By the plaque reduction assay, BU-2231 V was the most potent among the compounds tested, showing ID$_{50}$ of 0.84 mcg/ml. ε-poly-L-lysine and the higher molecular α-poly-L-lysine were slightly less active than BU-2231 V and the lower molecular α-poly-L-lysine was least active. By the dye-uptake assay, BU-2231 V and ε-poly-L-lysine were comparably active while the two α-poly-L-lysines were nearly inactive by this assay. BU-2231 V showed relatively weak cytotoxicity and had the best selectivity in this system.

(2) Antibacterial Activity

The in vitro antibacterial activity of BU-2231 V was determined by the 2-fold serial broth dilution method using nutrient broth in comparison with that of ε-poly-L-lysine and α-poly-L-lysine (MW:3,500). As shown in Table 3, these three compounds exhibited moderate inhibitory activity against Gram-positive and Gram-negative bacteria with a similar antibacterial spectrum. The antibacterial activities of BU-2231 V and ε-poly-L-lysine were comparable while the activity of α-poly-L-lysines was little weaker than others.

(3) Toxicity

The acute toxicity of (LD$_{50}$) BU-2231 V was 22.6 mg/kg by intramuscular administration into ddY mice.

TABLE 2

| | Activity against herpes simplex virus type I | | | |
|---|---|---|---|---|
| | Plaque reduction assay | | Dye-uptake assay | |
| | Activity vs HSV-1 (ID50:mcg/ml) | Cytotoxicity vs Vero cell (TCID50:mcg/ml) | Activity vs HSV-1 (ID50:mcg/ml) | Cytotoxicity vs Vero cell (TCID50:mcg/ml) |
| BU-2231V | 0.84 | 170 | 2.8 | 540 |
| ε-Poly-L-lysine | 2.6 | 70 | 2.7 | >100 |
| α-Poly-L-lysine (MW: 3,500) | 42 | >400 | 100 | >100 |
| α-Poly-L-lysine (MW: 25,000) | 1.8 | 25 | >20 | 20 |

TABLE 3

| | Antibacterial activity | | |
|---|---|---|---|
| | MIC by TDT (mcg/ml) | | |
| Test organisms | BU-2231V | ε-Poly-L-lysine | α-Poly-L-lysine |
| *Staphylococcus aureus* Smith | 6.3 | 6.3 | 12.5 |
| *Staphylococcus aureus* BX-1633-2 | 6.3 | 6.3 | 25 |
| *Streptococcus faecalis* A9612 | >100 | 50 | >100 |
| *Escherichia coli* Juhl | 6.3 | 6.3 | 12.5 |
| *Klebsiella pneumoniae* A9977 | 3.1 | 6.3 | 12.5 |
| *Proteus mirabilis* A9554 | 25 | 6.3 | 50 |
| *Serratia marcescens* A20019 | >100 | 25 | >100 |
| *Enterobacter cloacae* A9656 | 100 | 25 | >100 |
| *Haemophilus influenza* A2241 | 100 | 12.5 | 100 |
| *Pseudomonas aeruginosa* A9930 | 100 | 12.5 | >100 |

V. Partial Hydrolysis Products of BU-2231 V

In order to examine the relationship between peptide chain length and antiviral activity, a partial acid hydrolysis of BU-2231 V was carried out by heating with 6N HCl at 100 deg. C. for one hour. The hydrolyzate was chromatographed on CM-cellulose to yield 8 peptide fragments. Number of D-α,γ-diaminobutyric acid residues in each peptide was determined by the DNP method and antiviral activity against HSV-1 assessed by the dye-uptake assay (Table 4).

Fragment Nos. 6, 7 and 8 composing of more than 15 DAB residues showed a weak antiviral activity, while the peptide fragments having less than 12 DAB residues were practically inactive against HSV-1.

TABLE 4

Antiviral activity of partial hydrolyzates of BU-2231V

| Peptide Fragment No. | Number of DAB | Anti-HSV-1 activity ID50 (mcg/ml) |
|---|---|---|
| D-α,γ-DAB | 1 | >660 |
| 1 | 3–4 | " |
| 2 | 6–7 | " |
| 3 | 8–9 | " |
| 4 | 9–10 | " |
| 5 | 12–13 | " |
| 6 | 15–16 | 220 |
| 7 | 16–17 | 38 |
| 8 | 21–22 | 23 |
| BU-2231V | 51–52 | 2.8 |

VI. Method of Use and Pharmaceutical Composition

The antiviral antibiotic complex, BU-2231 V, according to the present invention and pharmaceutical compositions thereof are useful to inhibit the growth of Gram-positive and Gram-negative bacteria and of viruses, especially the herpes simplex virus. The antibacterial and antiviral effects of BU-2231 V was demonstrated as described above.

In general, BU-2231 V may be administered orally or parenterally in its pure solid form or in dilute solution or suspension or in a concentrate and prepared for unit dose or multi-dose presentation. When administered parenterally, by intravenous or intramuscular or subcutaneous injection, or when administered orally, the dosage administration will be dependent on the age and weight of the mammalian species being treated, the route of administration, and the type and severity of the infectious condition being presented or reduced.

The daily dosage for adult human treatment will preferably range from about 100 mg to about 1,000 mg for a 70 kg adult of the active BU-2231 V, depending on the nature of the infection and the frequency and route of administration inter alia. It will be appreciated that in some instances, e.g. in the treatment of neonates, infants and juveniles, smaller dosages than adult dosages may be desired.

The BU-2231 V pharmaceutical compositions thus will generally comprise a growth inhibitory amount (i.e. an amount effective to inhibit the growth of the virus or bacteria causing the condition of infection to be treated) of BU-2231 V in a suitable pharmaceutically acceptable carrier such as water, alcohols, fillers, stabilizers, wetting agents, emulsifying agents and dispersing agents to name but a few conventional carriers and adjuvants and excipients employed therewith.

The following example is illustrative of the present invention but is not to be construed to limit the scope of the invention.

EXAMPLE I

The fermentation of *Streptoalloteichus hindustanus* E465-94 was carried out as described in U.S. Pat. No. 4,051,237 and in H. Kawaguchi, *J. Antibiotics*, 30, 779-788 (1977). The harvested broth (3,000 L, pH 7.5) was centrifuged with the aid of a Sharpless centrifuge. The clear supernate obtained was applied on a column of Amberlite® IRC-50 resin (NH4, 300 L) which was developed with water (2,700 L), 0.01N NH4OH (1,200 L) and 0.25N NH4OH (300 L) successively and finally with 1.0N HCl (800 L) for elution of tallysomycins A and B. The antiviral activity was eluted with 0.25N NH4OH together with nebramycin components. The combined antiviral fractions were concentrated in vacuo and the residue was chromatographed on a column of Amberlite® CG-50 resin (NH4, 20 L). After being washed with water (30 L) and 0.05N NH4OH (30 L), the column was thoroughly developed with 0.1N NH4OH (46 L) to remove most of the nebramycin components. The eluant was then changed to 0.4N NH4OH and the eluates were monitored by TLC (SiO2, CHCl3-MeOH-28%NH4OH-H2O=1:4:2:1, v/v). The fractions nearly free from nebramycins were pooled, and concentrated to afford brownish solid pf cride BU-2231 V (1,094 g). An aqueous solution of this solid (130 g/5 L) was filtered and the filtrate was adjusted to pH 9.0 and charged on a column of Diaion ™ HP-20 resin (4 L). Elution was carried out with water (5 L) followed by 60% aqueous methanol, and the eluates were monitored by the TLC using the same solvent system as described above. The relevant fractions were concentrated in vacuo to give a semi-pure solid of BU-2231 V (9.6 g). This solid was chromatographed on a column of silica gel (Wako ™ C-200 gel, 3.0×65 cm), which was eluted with CHCl3-MeOH-28%NH4OH-H2O (1:4:2:1) and then with the upper layer of CHCl3-MeOH-28%NH4OH (1:1:1). The pooled active fractions were concentrated and applied on a column of Sephadex G-25 resin (2.0×65 cm). Upon development with water, the active eluates were combined, concentrated and lyophilized to give white solid of pure BU-2231 V complex (596 mg). The so-produced BU-2231 V complex was found to possess the structural and physico-chemical properties described above.

We claim:

1. The antiviral antibiotic complex designated BU-2231 V or a pharmaceutically acceptable acid addition salt thereof comprising a complex of γ-homopolymers of D-α,γ-diaminobutyric acid, which antibiotic complex when purified and lyophilized is in the form of a white amorphous solid having (1) a melting point of about 165–167 deg. C., (2) a specific optical rotation $[\alpha]^{25}$ of −19 deg. (c 1.0, H2O), (3) an elemental analysis corresponding to the formula $C_4H_8N_2O.1/3\ H_2CO_3$ of C-43.80% (43.08 calcd), H-7.84% (7.23 calcd), and N-23.00% (23.18 calcd), (4) an average molecular weight of about 5,700 when determined by gel filtration analysis and about 5,100–5,200 when determined by the dinitrophenylation method, and (5) an Rf value in thin layer chromatography analysis using silica gel of 0.02 with chloroform-methanol-28% aqueous ammonium hydroxide-water (1:4:2:1) and of 0.72 with chloroform-methanol-28% aqueous ammonium hydroxide, upper layer (1:1:1); which antibiotic complex is readily soluble in water and dimethyl sulfoxide, slightly soluble in methanol and ethanol, and only negligibly soluble in other organic solvents; which gives a positive response to ninhydrin, Dragendorff and Rydon-Smith reagents and a negative response to ferric chloride and anthrone reagents; which antibiotic complex gives an infrared spectrum substantially as shown in FIG. 1 which indicates amino (3400 $cm^{-1}$) and amide (1640 and 1540 $cm^{-1}$) functional groups when pelleted in potassium bromide and a high pressure liquid chromatographic spectrograph substantially as shown in FIG. 2; and which is effective in inhibiting growth of bacteria and viruses.

2. A pharmaceutical composition comprising (a) an amount effective to inhibit the growth of bacteria and viruses of the antiviral antibiotic complex BU-2231 V according to claim 1 and (b) a pharmaceutically acceptable carrier.

* * * * *